United States Patent
Cheng et al.

(10) Patent No.: US 11,986,149 B2
(45) Date of Patent: May 21, 2024

(54) PACKAGED IMAGE SENSOR AND ENDOSCOPE

(71) Applicant: Medimaging Integrated Solution, Inc., Hsinchu (TW)

(72) Inventors: Chu-Ming Cheng, Hsinchu (TW); Shangyi Wu, Hsinchu (TW)

(73) Assignee: MEDIMAGING INTEGRATED SOLUTION, INC., Hsinchu (TW)

( * ) Notice: Subject to any disclaimer, the term of this patent is extended or adjusted under 35 U.S.C. 154(b) by 370 days.

(21) Appl. No.: 17/407,784

(22) Filed: Aug. 20, 2021

(65) Prior Publication Data

US 2022/0265122 A1 Aug. 25, 2022

(30) Foreign Application Priority Data

Feb. 19, 2021 (TW) ................................ 110105870

(51) Int. Cl.
*A61B 1/00* (2006.01)
*A61B 1/05* (2006.01)
*A61B 1/06* (2006.01)

(52) U.S. Cl.
CPC .............. *A61B 1/0008* (2013.01); *A61B 1/05* (2013.01); *A61B 1/0684* (2013.01)

(58) Field of Classification Search
CPC ........ H04N 23/50; H04N 23/54; H04N 25/71; H04N 25/76; A61B 1/0008; A61B 1/05; A61B 1/0684; A61B 1/0011; A61B 1/0676; A61B 1/051; A61B 1/00124; A61B 1/005; A61B 1/0057
See application file for complete search history.

(56) References Cited

U.S. PATENT DOCUMENTS

| | | | |
|---|---|---|---|
| 6,920,883 B2 | 7/2005 | Bessette et al. | |
| 8,317,104 B2* | 11/2012 | Havens | H01L 27/14618 |
| | | | 235/454 |
| 9,496,247 B2 | 11/2016 | Oganesian et al. | |
| 11,309,299 B2* | 4/2022 | Wu | H05K 1/189 |
| 2010/0200898 A1* | 8/2010 | Lin | H01L 31/0203 |
| | | | 257/E31.11 |
| 2018/0125335 A1* | 5/2018 | Motohara | H01L 27/14 |
| 2019/0013444 A1 | 1/2019 | Morimoto et al. | |
| 2019/0208143 A1* | 7/2019 | Brooks | A61B 1/00183 |
| 2022/0365334 A1* | 11/2022 | Igarashi | H04N 25/709 |
| 2023/0148836 A1* | 5/2023 | Levy | A61B 1/0661 |
| | | | 348/76 |

FOREIGN PATENT DOCUMENTS

EP 3013209 B1 7/2020

* cited by examiner

*Primary Examiner* — Kelly L Jerabek
(74) *Attorney, Agent, or Firm* — Muncy, Geissler, Olds & Lowe, P.C.

(57) ABSTRACT

A packaged image sensor includes a first pipe and a second pipe, wherein the first pipe with a shorter length is initially encapsulated with an image sensor and a light-emitting element to define a relative position between the first pipe and the image sensor. The second pipe is connected to the first pipe and then is encapsulated in a second encapsulation process. The abovementioned packaged image sensor is easy to manufacture. An endoscope including the abovementioned packaged image sensor is also disclosed.

22 Claims, 7 Drawing Sheets

Fig. 7

PACKAGED IMAGE SENSOR AND ENDOSCOPE

BACKGROUND OF THE INVENTION

1. Field of the Invention

The present invention relates to a packaged image sensor and an endoscope, particularly to a packaged image sensor including a working channel and an endoscope using the same.

2. Description of the Prior Art

Endoscopes can reach the cavities of an object, which the naked eyes are unlikely to observe directly, and capture images therefrom. Therefore, endoscopes have been extensively used in industry and medicine. The application of endoscopes particularly has significant influence in medicine. Endoscopes are required to access target cavities of human bodies through various small channels. For an example, a bronchoscope accesses the lung through a bronchial. For another example, a cystoscope accesses the bladder through the urethra. Hence, miniaturizing an endoscope is an important subject of the concerned field.

Figure 1:
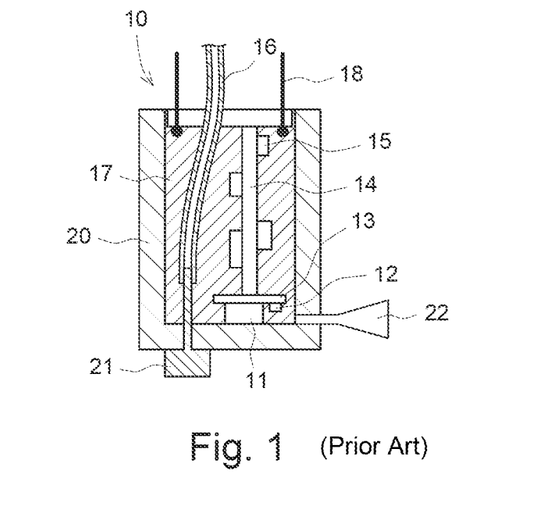
FIG. 1 and FIG. 2 are diagrams schematically showing a conventional image sensor module of an endoscope.
Figure 2:
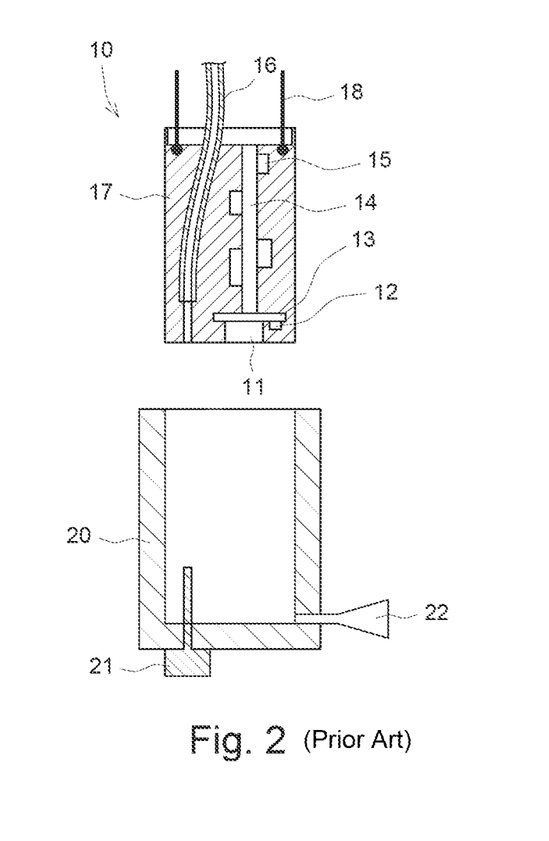

Refer to FIG. 1 and FIG. 2. In an image sensing module 10 of a conventional endoscope, an image sensing element 11 and a light-emitting element 12 are disposed on a substrate 13. The other side of the substrate 13 is connected with a circuit board 14. The circuit board 14 has electronic elements 15. The abovementioned elements are placed inside a mold chase 20. A pipe 16 functioning as a working channel sleeves a protrudent element 21 inside the mold chase 20, whereby to fix the relative position of the pipe 16 and the image sensing element 11. Next, an encapsulant 17 is filled into the mold chase 20 through a filling hole 22. After the encapsulant 17 is cured, demolding is undertaken to obtain the image sensing module 10.

As shown in FIG. 1 and FIG. 2, the pipe 16, which is connected with an operating end, tightly sleeves the protrudent element 21 inside the mold chase 20, and the aspect ratio of the mold chase 20 is relatively larger, which will lead to difficulty of demolding. Besides, a plurality of steering control wires 18, which are used to steer the image sensing module 10, is connected to the proximal end of the image sensing module 10. In other words, the steering control wires 18 is far away from the top end of the image sensing module 10. Thus, the image sensing module 10 has a larger bending radius, which will inconvenience operation. For example, the distance between the top end of the image sensing module 10 and the connection position of the steering control wires 18 is about 10 to 12 mm.

Accordingly, the manufacturers are eager to develop an endoscope that is easy to fabricate.

SUMMARY OF THE INVENTION

The present invention proposes a packaged image sensor and an endoscope using the same, wherein a preliminary encapsulation process is undertaken to encapsulate a shorter first pipe, an image sensor and a light-emitting element to fix the relative position of the first pipe and the image sensor; a second pipe, which extends to an operating end, is joined to the first pipe and encapsulated in a second encapsulation process, whereby to simplify mold chase design and make tool releasing easier.

In one embodiment, the packaged image sensor of the present invention comprises a substrate, an image sensor, a light-emitting element, a first encapsulant, a circuit board, a plurality of conductive wires, a first pipe, and a second encapsulant. The substrate includes a plurality of first electric-conduction contacts, a plurality of second electric-conduction contacts, and a plurality of third electric-conduction contacts, wherein the plurality of second electric-conduction contacts and the plurality of third electric-conduction contacts are electrically connected with the plurality of corresponding first electric-conduction contacts. The image sensor is disposed on the substrate and electrically connected with the plurality of second electric-conduction contacts. The light-emitting element is disposed on the substrate and near the image sensor. The light-emitting element is electrically connected with the plurality of third electric-conduction contacts. The first encapsulant is filled into a space between the image sensor and the light-emitting element. The circuit board includes a plurality of fourth electric-conduction contacts and a plurality of fifth electric-conduction contacts. The plurality of fourth electric-conduction contacts are electrically connected with the plurality of corresponding first electric-conduction contacts of the substrate. The plurality of conductive wires are electrically connected with the plurality of corresponding fifth electric-conduction contacts of the circuit board. The end of an opening of the first pipe faces a sensing direction of the image sensor and is arranged beside the substrate. The second encapsulant encapsulates the substrate, the circuit board, one end of the plurality of conductive wires, and a portion of the first pipe, and keeps two ends of the first pipe opened.

In one embodiment, the endoscope of the present invention comprises a tube, a packaged image sensor, and an electric connector. The tube includes a first opening and a second opening. The end of the first opening of the tube is put into a cavity. The packaged image sensor is disposed at the end of the first opening of the tube to capture images of the cavity and generate corresponding signals. The packaged image sensor includes a substrate, an image sensor, a light-emitting element, a first encapsulant, a circuit board, a plurality of conductive wires, a first pipe, a second encapsulant, a second pipe, and a third encapsulant. The substrate further includes a plurality of first electric-conduction contacts, a plurality of second electric-conduction contacts, and a plurality of third electric-conduction contacts, wherein the plurality of second electric-conduction contacts and the plurality of third electric-conduction contacts are electrically connected with the plurality of corresponding first electric-conduction contacts. The image sensor is disposed on the substrate and electrically connected with the plurality of second electric-conduction contacts. The light-emitting element is disposed on the substrate and near the image sensor. The light-emitting element is electrically connected with the plurality of third electric-conduction contacts. The first encapsulant is filled into a space between the image sensor and the light-emitting element. The circuit board includes a plurality of fourth electric-conduction contacts and a plurality of fifth electric-conduction contacts. The plurality of fourth electric-conduction contacts are electrically connected with the plurality of corresponding first electric-conduction contacts of the substrate. The plurality of conductive wires are electrically connected with the plurality of corresponding fifth electric-conduction contacts of the circuit board. The end of an opening of the first pipe faces a sensing direction of the image sensor and is arranged beside the substrate. The second encapsulant encapsulates the substrate, the circuit board, one end of the plurality of conductive wires, and a portion of the first pipe, and keeps two ends of the first pipe opened. The second pipe is joined to the first pipe to function as a working channel. The third encapsulant encapsulates the light-emitting element, the second encapsulant and a connection end of the second pipe. The electric connector is disposed at an end of the second opening of the tube and electrically connected with the other end of the plurality of conductive wires, whereby the endoscope can be electrically connected with an external electronic device in a pluggable way.

The objective, technologies, features and advantages of the present invention will become apparent from the following description in conjunction with the accompanying drawings wherein certain embodiments of the present invention are set forth by way of illustration and example.

BRIEF DESCRIPTION OF THE DRAWINGS

The foregoing conceptions and their accompanying advantages of this invention will become more readily appreciated after being better understood by referring to the following detailed descriptions, in conjunction with the accompanying drawings, wherein.

DESCRIPTION OF THE PREFERRED EMBODIMENTS

Various embodiments of the present invention will be described in detail below and illustrated in conjunction with the accompanying drawings. In addition to these detailed descriptions, the present invention can be widely implemented in other embodiments, and apparent alternations, modifications and equivalent changes of any mentioned embodiments are all included within the scope of the present invention and based on the scope of the Claims. In the descriptions of the specification, in order to have a more complete understanding about the present invention, many specific details are provided; however, the present invention may be implemented without parts of or all the specific details. In addition, the well-known steps or elements are not described in detail, in order to avoid unnecessary limitations to the present invention. Same or similar elements in Figures will be indicated by same or similar reference numbers. It is noted that the Figures are schematic and may not represent the actual size or number of the elements. For clearness of the Figures, some details may not be fully depicted.

Figure 3:
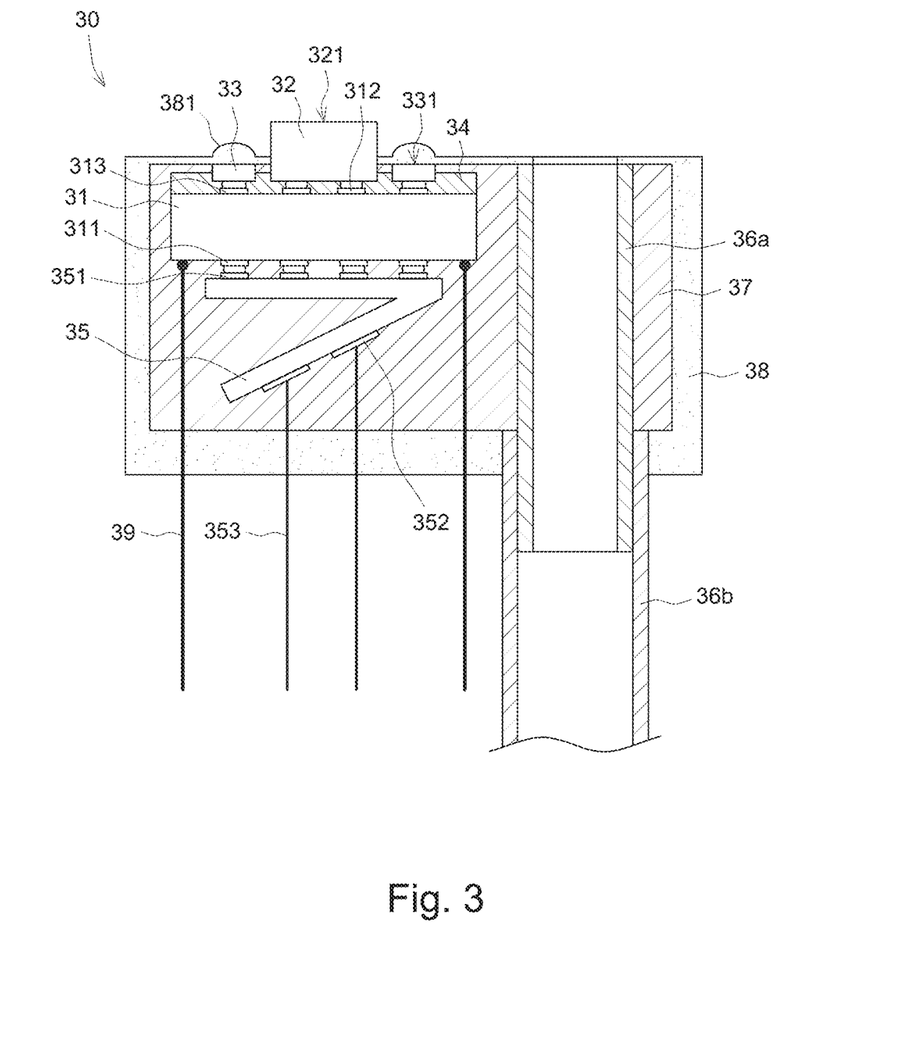
FIG. 3 is a diagram schematically showing a packaged image sensor according to a first embodiment of the present invention.

Refer to FIG. 3. In one embodiment, the packaged image sensor 30 of the present invention comprises a substrate 31, an image sensor 32, a light-emitting element 33, a first encapsulant 34, a circuit board 35, a plurality of conductive wires 353, a first pipe 36a, and a second encapsulant 37. The substrate 31 includes a plurality of first electric-conduction contacts 311, a plurality of second electric-conduction contacts 312, and a plurality of third electric-conduction contacts 313, wherein the plurality of second electric-conduction contacts 312 and the plurality of third electric-conduction contacts 313 are electrically connected with the plurality of corresponding first electric-conduction contacts 311. In one embodiment, the plurality of second electric-conduction contacts 312 and the plurality of third electric-conduction contacts 313 are disposed on one side opposite to the plurality of first electric-conduction contacts 311. In one embodiment, the substrate 31 is a ceramic substrate.

The image sensor 32 is disposed on the substrate 31 and electrically connected with the corresponding second electric-conduction contacts 322. The light-emitting element 33 is disposed on the substrate 31 and near the image sensor 32. The light-emitting element 33 is electrically connected with the corresponding third electric-conduction contacts 313. In one embodiment, the packaged image sensor 30 comprises a plurality of light-emitting elements 33. The plurality of light-emitting elements 33 may respectively emit light beams having different wavelengths or spectrums. The plurality of light-emitting elements 33 may be simultaneously or separately operated to observe different targets or objects. It is easily understood: the plurality of light-emitting elements 33 may emit light beams having the same wavelength for illumination or other different purposes. For example, the light-emitting elements 33 may be white light-emitting diodes (LED), infrared LEDs, blue LED, ultraviolet LEDs, or a combination thereof.

The first encapsulant 34 is filled into the space between the image sensor 32 and the light-emitting element 33. In one embodiment, the first encapsulant 34 is made of a semi-transparent or opaque resin, whereby to protect the imaging system of the image sensor 32 from being influenced by the illumination light or stray light, which is emitted by the light-emitting element 33. For example, the semi-transparent resin may have a transmittance of 0.01 to 50%. It is easily understood: the light-output surface 331 of the light-emitting element 33 must be higher than the top surface of the first encapsulant 34 lest the light output of the light-emitting element 33 be influenced. In other words, the first encapsulant 34 cannot cover the light-output surface 331 of the light-emitting element 33.

The circuit board 35 includes a plurality of fourth electric-conduction contacts 351 and a plurality of fifth electric-conduction contacts 352. The plurality of fourth electric-conduction contacts 351 are electrically connected with the plurality of corresponding first electric-conduction contacts 311 of the substrate 31. In one embodiment, the circuit board 35 may be a printed circuit board (PCB) or a flexible printed circuit (FPC). The plurality of conductive wires 353 are electrically connected with the plurality of corresponding fifth electric-conduction contacts 352 of the circuit board 35. The plurality of conductive wires 353 may act or work as power wires and signal transmission wires, whereby the packaged image sensor 30 may be electrically connected with the exterior. For an example, the packaged image sensor 30 may be connected with a power supply or transmit image signals to a rear-end controller or a display device.

The end of an opening of the first pipe 36a faces a sensing direction of the image sensor 32 and is arranged beside the substrate 31. For example, the opening of the first pipe 36 is extended to the area where the image sensor 32 will detect. The second encapsulant 37 encapsulates the substrate 31, the circuit board 35, one end of the plurality of conductive wires 353, and a portion of the first pipe 36a. For example, the end of the other opening of the first pipe 36a protrudes from the second encapsulant 37. It is easily understood: the second encapsulant 37 is not allowed to cover two openings at two ends of the first pipe 36a so as to keep two ends of the first pipe 36a opened. It should be explained: the second encapsulant 37 may be built in two encapsulation steps. For example, the second encapsulant 37 is used to encapsulate one end of the plurality of conductive wires 353 in advance, and then the second encapsulant 37 is used to encapsulate the first pipe 36a and the substrates 31.

Refer to FIG. 3 again. In one embodiment, the packaged image sensor 30 further comprises a second pipe 36b and a third encapsulant 38. One end of the second pipe 36b is joined to the first pipe 36a; another end of the second pipe 36b is extended to the operating end, whereby the second pipe 36b may be functional as a working channel. The operator may put a working instrument to a cavity through the second pipe 36b, which acts as the working channel, to undertake an intended work, such as sampling tissue, sucking out secretions/tissue fluids/blood, or supplying medicine. The third encapsulant 38 encapsulates the light-emitting element 33 and the second encapsulant 37. The third encapsulant 38 also encapsulates the connection end of the second pipe 36 lest the second pipe 36b be separated from the first pipe 36a. In one embodiment, the third encapsulant 38 includes a secondary optical structure 381. The secondary optical structure 381 is disposed on the light-output side of the light-emitting element 33. The secondary optical structure 381 can adjust the light-exiting angle so as to increase the utilization rate or extraction ratio of illumination and the distance of illumination.

According to the disclosed structure above, the first pipe 36a is used to join with the second pipe 36b. Therefore, the first pipe 36a is shorter in length. Thus, the mold of the first encapsulation may be simplified to make the mold releasing easier. After the preliminary encapsulation for the first pipe 36a and the substrate 31, the relative position of the first pipe 36a and the image sensor 32 is fixed. Thus, in the succeeding encapsulation second pipe 36b that has been joined to the first pipe 36a, the mold chase doses not need an additional design to fix the second pipe 36b. Therefore, the mold for the second encapsulation may also be simplified to make the mold releasing easier.

Refer to FIG. 3 again. In one embodiment, the packaged image sensor 30 further comprises a plurality of steering control wires 39, which are connected with the substrate 31. The second encapsulant 37 encapsulates one end of the steering control wires 39 lest the steering control wires 39 be detached from the substrate 31. In the embodiment shown in FIG. 3, the steering control wires 39 are connected with the substrate 31. However, the present invention is not limited by the embodiment. For example, the steering control wires 39 may be connected with the circuit board 35. In one embodiment, the steering control wires 39 are connected with the substrate 31 via soldering, welding or snap-fitting, and the second encapsulant 37 is used to cover the position where the steering control wires 39 are connected lest the steering control wires 39 be separated from the substrate 31.

The packaged image sensor 30 may be steered by pulling the steering control wires 39. In one embodiment, the first pipe 36a, the second encapsulant 37 and the third encapsulant 38 are made of flexible materials. Based on the disclosed structure above, only the substrate 31 and the image sensor 32 are unbent along the optical axis. Thus, the bending radius of the packaged image sensor 30 of the present invention is significantly improved. Therefore, the present invention can be applied to a situation needing a smaller bending radius.

Figure 4:
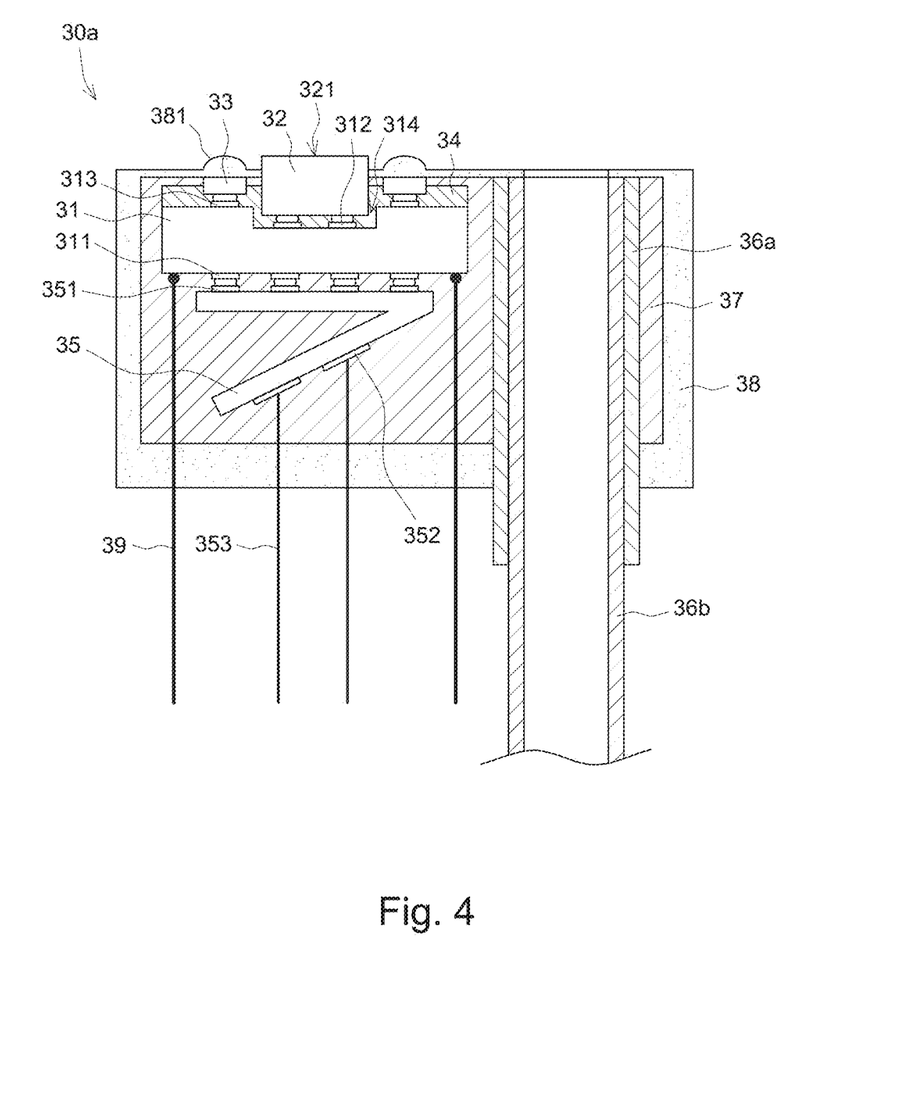
FIG. 4 is a diagram schematically showing a packaged image sensor according to a second embodiment of the present invention.

In the embodiment shown in FIG. 3, the second pipe 36b sleeves one end of the first pipe 36a. As shown in FIG. 3, the inner surfaces of the first pipe 36a and the second pipe 36b are not coplanar. In one embodiment, a connection structure is disposed at the joint of the first pipe 36a and the second pipe 36b to make the inner surfaces of the first pipe 36a and the second pipe 36b coplanar. In other words, the inner surfaces of the first pipe 36a and the second pipe 36b are joined to each other to form a smooth surface. For example, a stage-difference structure or inclines surfaces may be arranged in the joint of the first pipe 36a and the second pipe 36b. Refer to FIG. 4. Alternatively, the second pipe 36b may be completely placed inside the first pipe 36a to make the second pipe 36b extend from the operating end to the end of the opening of the packaged image sensor 30a. Thus, the inner surface of the working channel is a continuous surface, i.e. a smooth surface, from the operating end to the end of the opening of the packaged image sensor 30a.

It is easily understood: the relative altitude of the image sensor 32 and the light-emitting element 33 may influence the illumination and the imaging quality. For example, if the light-output surface 331 of the light-emitting element 33 is relatively too low with respect to the image sensor 32, the image sensor 32 may block the illuminating light emitted by the light-emitting element 33 and generate shadows; if the light-input surface 321 of the image sensor 32 is relatively too low with respect to the light-emitting element 33, the light-emitting element 33 may block the imaging light reflected by the inspected object; alternatively, the illuminating light emitted by the light-emitting element 33 may directly enter the image sensor 32 and affect the imaging quality. In one embodiment, the altitude of the light-input surface 321 of the image sensor 32 is equal to or higher than the altitude of the light-output surface 331 of the light-emitting element 33. It is preferred: the difference between the altitude of the light-input surface 321 of the image sensor 32 and the altitude of the light-output surface 331 of the light-emitting element 33 is equal to or smaller than 0.5 mm. Refer to FIG. 4. In one embodiment, the substrate 31 includes a recess 314; the plurality of second electric-conduction contacts 312 and the image sensor 32 are disposed on the bottom of the recess 314. Based on the disclosed structure above, the relative position of the light-input surface 321 of the image sensor 32 and the light-output surface 331 of the light-emitting element 33 may be controlled by adjusting the depth of the recess 314, whereby to optimize the illumination quality and the imaging quality.

Figure 5:
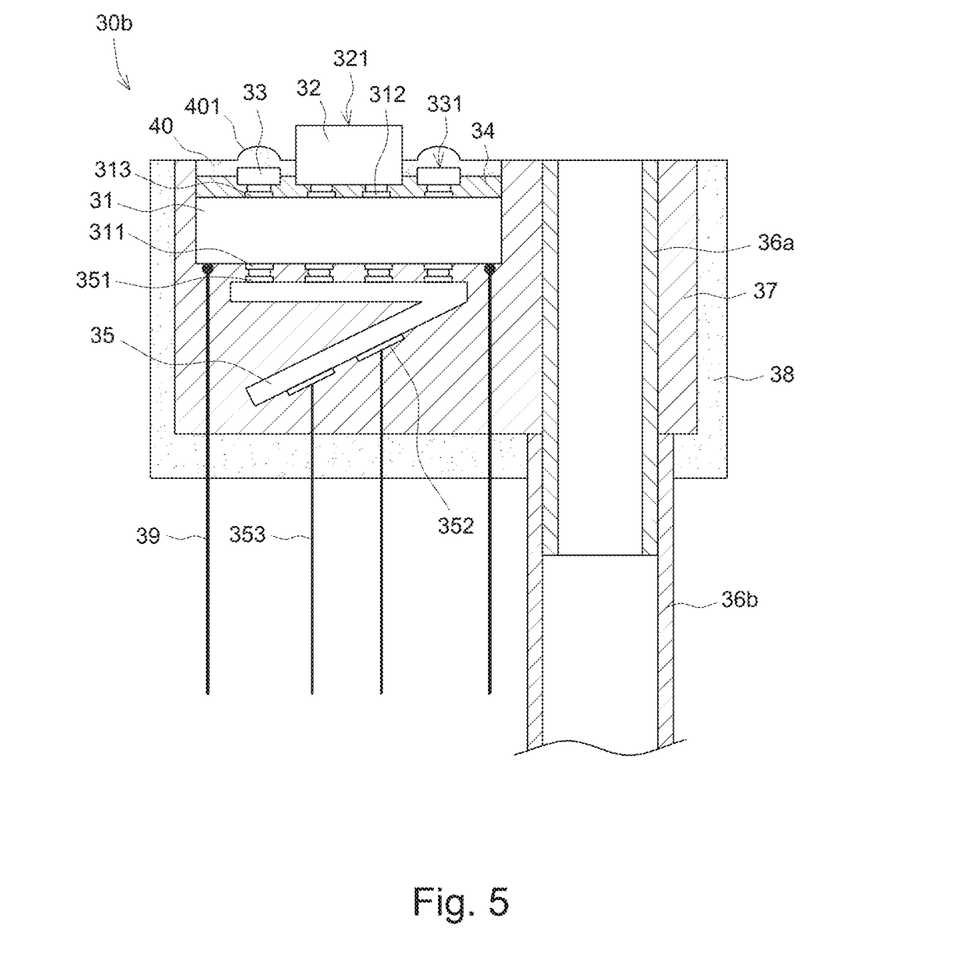
FIG. 5 is a diagram schematically showing a packaged image sensor according to a third embodiment of the present invention.

Refer to FIG. 5. In one embodiment, the secondary optical structure 401 of the packaged image sensor 30b may be independent from the third encapsulant 38. For example, in the state that the substrate 31 is not cut yet, a resin 40 may be used to form the secondary optical structure 401 on the substrate 31 beforehand. After cutting the substrate 31, connecting the circuit board 35 and disposing the first pipe 36a, the second encapsulant 37 is used to complete the first encapsulation process. Next, the second pipe 36b is joined to the first pipe 36a, and the third encapsulant 38 is used to complete the second encapsulation process. In one embodiment, the third encapsulant 38 is preferably made of a highly transparent resin.

Figure 6A:
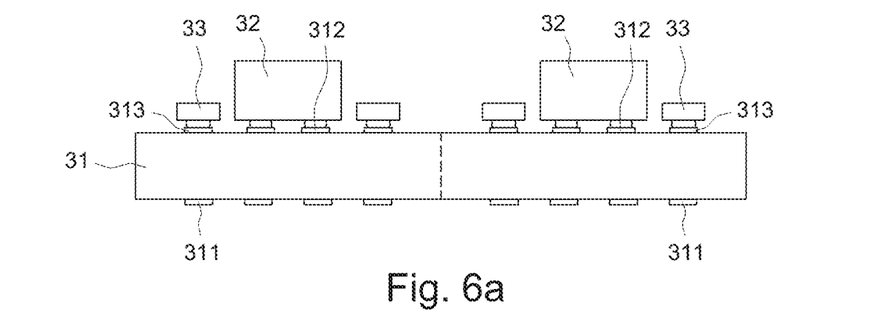
FIGS. 6a-6e are diagrams schematically showing a method for fabricating a packaged image sensor according to one embodiment of the present invention.

Refer to FIGS. 6a-6e for a method of fabricating the packaged image sensor 30 shown in FIG. 3. Refer to FIG. 6a. Firstly, provide a substrate. The substrate includes a plurality of substrates 31 arranged in array, a plurality of first electric-conduction contacts 311, a plurality of second electric-conduction contacts 312, and a plurality of third electric-conduction contacts 313, wherein the first electric-conduction contacts 311, the second electric-conduction contacts 312 and the third electric-conduction contacts 313 are corresponding to the substrates 31. The image sensors 32 are joined with the substrates 31 in a die-bonding method and electrically connected with the corresponding second electric-conduction contacts 312. The light-emitting elements 33 are also disposed on the substrates 31 and electrically connected with the corresponding third electric-conduction contacts 313.

Figure 6B:
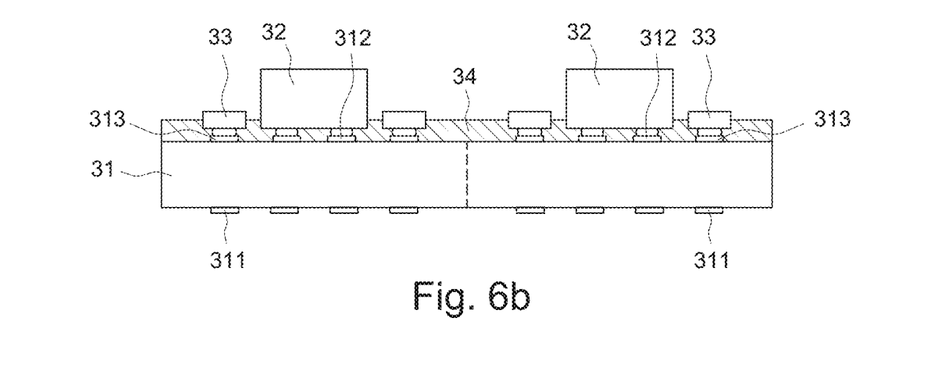

Refer to FIG. 6b. Next, fill the first encapsulant 34 into a space between the image sensors 32 and the light-emitting elements 33, and cure the first encapsulant 34 by an ultraviolet method, a thermal method or another appropriate method. It is easily understood: while the packaged image sensor 30b shown in FIG. 5 is to be fabricated, the secondary optical structure 401 must be formed with the resin 40 beforehand. Next, cut the substrate along the cutting alignment marks or the cutting lines (such as the dashed line shown in FIG. 6b) to generate separated image sensor modules, wherein each image sensor module includes the image sensor 32 and the light-emitting element 33.

Figure 6C:
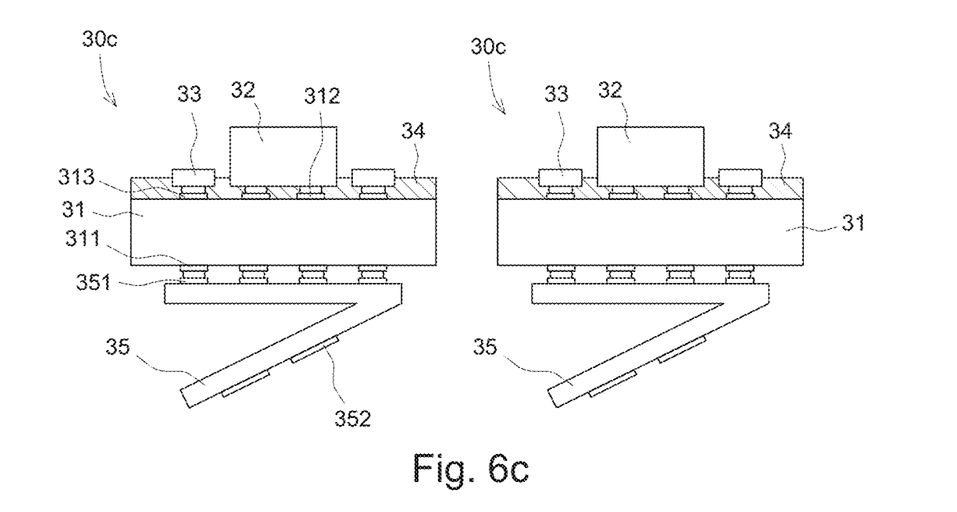
Figure 6D:
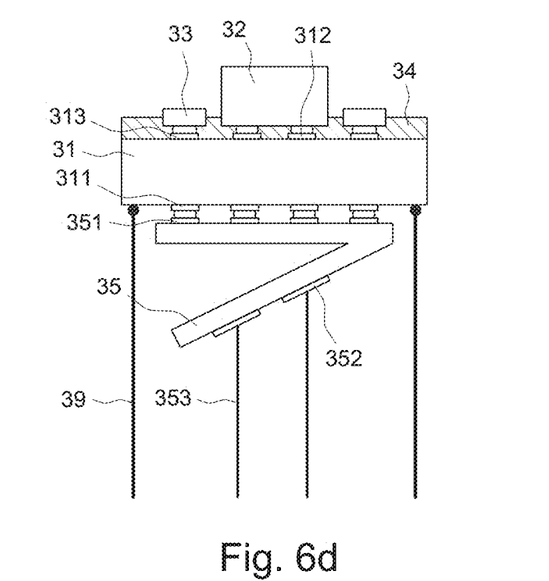

Refer to FIG. 6c. Next, dispose the separated image sensor module 30c on the circuit board 35 in a surface mount technology (SMT) or another appropriate technology, and electrically connect the image sensor module 30c with the circuit board 35. Refer to FIG. 6d. Next, electrically connect a plurality of conductive wires 353 with the corresponding fifth electric-conduction contacts 352 of the circuit board 35, and join the steering control wires 39 to the substrate 31.

Figure 6E:
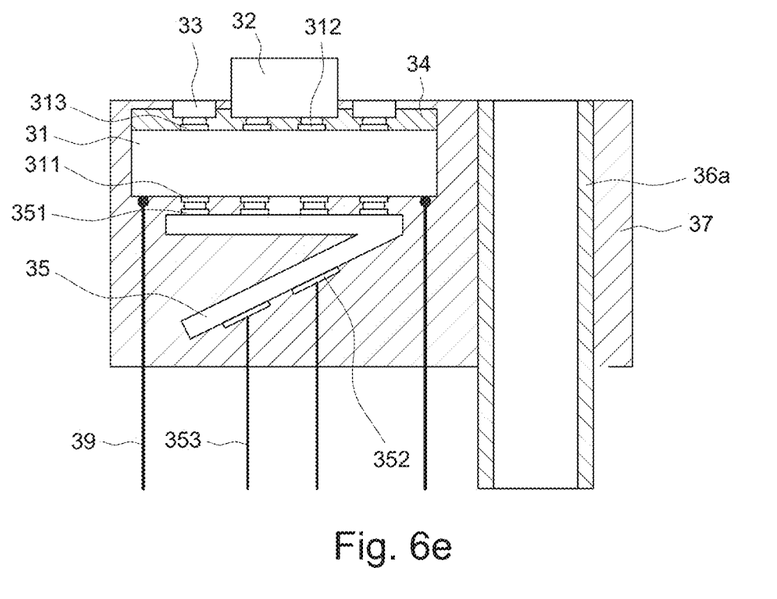

Refer to FIG. 6e. Next, place the image sensor module shown in FIG. 6d and the first pipe 36a in an appropriate mold chase, and fill the second encapsulant 37 into the mold chase to fix the relative position of the first pipe 36a and the image sensor 32 to form an image sensor module. Then, place the image sensor module shown in FIG. 6e in another appropriate mold chase, and fill the third encapsulant 38 into the mold chase to form the secondary optical structures 381 on the light-output sides of the light-emitting elements 33, and the packaged image sensor 30 shown in FIG. 3 was completed. It is easily understood: if the independent secondary optical structures 401 shown in FIG. 5 have been fabricated beforehand, this step needn't fabricate the secondary optical structures 381.

Figure 7:
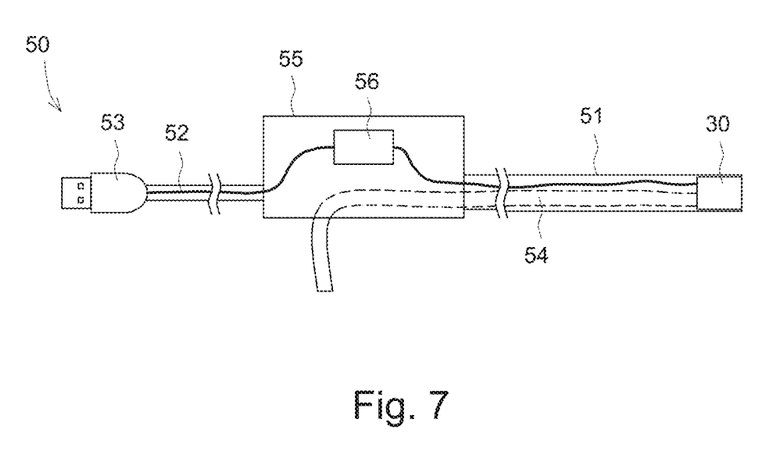
FIG. 7 is a diagram schematically showing an endoscope according to one embodiment of the present invention.

Refer to FIG. 7. In one embodiment, the endoscope 50 of the present invention comprises a tube 51, a packaged image sensor 30, a plurality of conductive wires 52, an electric connector 53 and a working channel 54. The tube 51 includes a first opening and a second opening. The end of the first opening of the tube 51 of the endoscope 50 is put into a cavity, such as a cavity of a human body or a small space to be inspected in an industrial inspection. It is easily understood: the tube 51 may be designed to have different appearances to satisfy with applications. The packaged image sensor 30 is disposed at the first opening of the tube 51, whereby to capture images of a cavity and generate corresponding signals. The detailed structure of the packaged image sensor 30 has been described hereinbefore and will not repeat again. The pipe 36b of the packaged image sensor 30 shown in FIG. 3 is extended to form the working channel 54. The operator may put a working instrument through the working channel 54 into a cavity to undertake an intended work, such as sampling tissue, sucking out secretions/tissue fluids/blood, or supplying medicine.

The conductive wires 52 are respectively electrically connected with the packaged image sensor 30 and the electric connector 53, whereby the electronic signals generated by the packaged image sensor 30 may be transmitted to an external electronic device, such as a computer, a mobile Internet-access device or a dedicated electronic device of the endoscope, through the electric connector 53. In one embodiment, the electric connector 53 is electrically connected with an external electronic device in a pluggable way. The electric connector 53 may be a USB interface, a connection interface of a mobile Internet-access device or another appropriate electric connector.

In one embodiment, the endoscope 50 of the present invention further comprises a housing 55. The housing 55 is disposed between the tube 51 and the electric connector 53. The design of the housing 55 may be varied according to requirement. For an example, the housing 55 may have an appearance suitable to be held by the operator. For another example, the shape of the housing 55 is suitable to be mounted on a carrier, such as a head-mounted carrier. In one embodiment, the endoscope 50 of the present invention further comprises an electronic element 56. The electronic element 56 is electrically connected with the packaged image sensor 30 and the electric connector 53. The electronic element 56 can process the electronic signals generated by the packaged image sensor 30 and transmit the electronic signals to an external electronic device through the electric connector 53. In one embodiment, the electronic element 56 is a microcontroller unit (MCU).

In conclusion, the present invention proposes a packaged image sensor and an endoscope using the same, wherein the preliminary encapsulation process is undertaken to encapsulate the shorter first pipe, the image sensor and the light-emitting element to fix the relative position of the first pipe and the image sensor; the second pipe, which extends to the operating end, is joined to the first pipe and then encapsulated in the second encapsulation process, whereby to simplify mold chase design and make demolding easier. The steering control wires are joined to the substrate or the circuit board. Besides, the first pipe and the encapsulants are made of flexible materials. Therefore, the packaged image sensor and the endoscope using the same may have a smaller bending radius and are applicable to a narrower space where a smaller bending radius is required.

While the invention is susceptible to various modifications and alternative forms, a specific example thereof has been shown in the drawings and is herein described in detail. It should be understood, however, that the invention is not to be limited to the particular form disclosed, but to the contrary, the invention is to cover all modifications, equivalents, and alternatives falling within the appended claims.

What is claimed is:

1. A packaged image sensor, comprising:
 a substrate, including a plurality of first electric-conduction contacts, a plurality of second electric-conduction contacts, and a plurality of third electric-conduction contacts, wherein the plurality of second electric-conduction contacts and the plurality of third electric-conduction contacts are electrically connected with the plurality of corresponding first electric-conduction contacts;
 an image sensor, disposed on the substrate and electrically connected with the plurality of second electric-conduction contacts;
 a light-emitting element, disposed on the substrate and near the image sensor and electrically connected with the plurality of third electric-conduction contacts;

a first encapsulant, filled into a space between the image sensor and the light-emitting element;

a circuit board, including a plurality of fourth electric-conduction contacts and a plurality of fifth electric-conduction contacts, wherein the plurality of fourth electric-conduction contacts is electrically connected with the plurality of corresponding first electric-conduction contacts of the substrate;

a plurality of conductive wires, electrically connected with the plurality of corresponding fifth electric-conduction contacts;

a first pipe, wherein an end of an opening of the first pipe faces a sensing direction of the image sensor and is arranged beside the substrate; and a second encapsulant, encapsulating the substrate, the circuit board, one end of the plurality of conductive wires and a portion of the first pipe, and keeping two ends of the first pipe opened.

2. The packaged image sensor according to claim 1, further comprising:

a second pipe, joined to the first pipe and acting as a working channel; and a third encapsulant, encapsulating the light-emitting element, the second encapsulant, and a connection end of the second pipe.

3. The packaged image sensor according to claim 2, wherein the third encapsulant includes a secondary optical structure corresponding to the light-emitting element.

4. The packaged image sensor according to claim 1, further comprising:

a secondary optical structure, disposed on a light-output side of the light-emitting element.

5. The packaged image sensor according to claim 1, further comprising:

a plurality of steering control wires, which is connected with the substrate or the circuit board, wherein the second encapsulant encapsulates one end of the steering control wires.

6. The packaged image sensor according to claim 5, wherein the second encapsulant is flexible.

7. The packaged image sensor according to claim 5, wherein the first pipe is flexible.

8. The packaged image sensor according to claim 1, wherein the substrate includes a recess; the plurality of second electric-conduction contacts and the image sensor are disposed on a bottom of the recess.

9. The packaged image sensor according to claim 1, wherein an altitude of a light-input surface of the image sensor is equal to or higher than an altitude of a light-output surface of the light-emitting element.

10. The packaged image sensor according to claim 1, wherein the packaged image sensor comprises a plurality of the light-emitting elements; the plurality of light-emitting elements emit light beams having an identical wavelength or respectively emits light beams having different wavelengths or spectrums.

11. The packaged image sensor according to claim 1, wherein the first encapsulant is made of a semi-transparent resin or an opaque resin.

12. An endoscope, comprising:

a tube, including a first opening and a second opening, wherein an end of the first opening of the tube is to be put into a cavity;

an packaged image sensor, disposed at the end of the first opening of the tube, used to capture images of the cavity and generate corresponding electronic signals, and including:

a substrate, including a plurality of first electric-conduction contacts, a plurality of second electric-conduction contacts, and a plurality of third electric-conduction contacts, wherein the plurality of second electric-conduction contacts and the plurality of third electric-conduction contacts are electrically connected with the plurality of corresponding first electric-conduction contacts;

an image sensor, disposed on the substrate and electrically connected with the plurality of second electric-conduction contacts;

a light-emitting element, disposed on the substrate and near the image sensor and electrically connected with the plurality of third electric-conduction contacts;

a first encapsulant, filled into a space between the image sensor and the light-emitting element;

a circuit board, including a plurality of fourth electric-conduction contacts and a plurality of fifth electric-conduction contacts, wherein the plurality of fourth electric-conduction contacts are electrically connected with the plurality of corresponding first electric-conduction contacts of the substrate;

a plurality of conductive wires, electrically connected with the plurality of corresponding fifth electric-conduction contacts of the circuit board;

a first pipe, wherein an end of an opening of the first pipe faces a sensing direction of the image sensor and is arranged beside the substrate;

a second encapsulant, encapsulating the substrate, the circuit board, one end of the plurality of conductive wires and a portion of the first pipe, and keeping two ends of the first pipe opened;

a second pipe, joined to the first pipe and acting as a working channel; and a third encapsulant, encapsulating the light-emitting element, the second encapsulant, and a connection end of the second pipe; and an electric connector, disposed at an end of the second opening of the tube, electrically connected with another end of the plurality of conductive wires, enabling the endoscope to be electrically connected with an external electronic device in a pluggable way.

13. The endoscope according to claim 12, further comprising:

an electronic element, electrically connected with the packaged image sensor and the electric connector and processing electronic signals generated by the packaged image sensor.

14. The endoscope according to claim 12, further comprising:

a housing, disposed between the packaged image sensor and the electric connector.

15. The endoscope according to claim 12, wherein the packaged image sensor further comprises:

a secondary optical structure, disposed on a light-output side of the light-emitting element.

16. The endoscope according to claim 12, wherein the packaged image sensor further comprises:

a plurality of steering control wires, which is connected with the substrate or the circuit board, wherein the second encapsulant encapsulates one end of the steering control wires.

17. The endoscope according to claim 16, wherein the second encapsulant is flexible.

18. The endoscope according to claim 16, wherein the first pipe is flexible.

19. The endoscope according to claim 12, wherein the substrate includes a recess; the plurality of second electric-conduction contacts and the image sensor are disposed on a bottom of the recess.

20. The endoscope according to claim 12, wherein an altitude of a light-input surface of the image sensor is equal to or higher than an altitude of a light-output surface of the light-emitting element.

21. The endoscope according to claim 12, wherein the packaged image sensor comprises a plurality of the light-emitting elements; the plurality of light-emitting elements emits light beams having an identical wavelength or respectively emits light beams having different wavelengths or spectrums.

22. The endoscope according to claim 12, wherein the first encapsulant is made of a semi-transparent resin or an opaque resin.

\* \* \* \* \*